(12) United States Patent
Zhang et al.

(10) Patent No.: US 11,111,265 B2
(45) Date of Patent: Sep. 7, 2021

(54) METHOD FOR PREPARING CHOLIC ACID COMPOUND

(71) Applicant: Chia Tai Tianqing Pharmaceutical Group Co., Ltd., Lianyungang (CN)

(72) Inventors: Xiquan Zhang, Lianyungang (CN); Xingdong Cheng, Lianyungang (CN); Aiming Zhang, Lianyungang (CN); Chunguang Xia, Lianyungang (CN); Lang Chen, Lianyungang (CN); Ce Gao, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 52 days.

(21) Appl. No.: 16/759,134

(22) PCT Filed: Nov. 1, 2018

(86) PCT No.: PCT/CN2018/113326
§ 371 (c)(1),
(2) Date: Apr. 24, 2020

(87) PCT Pub. No.: WO2019/085963
PCT Pub. Date: May 9, 2019

(65) Prior Publication Data
US 2020/0347091 A1   Nov. 5, 2020

(30) Foreign Application Priority Data

Nov. 2, 2017   (CN) .......................... 201711062367.6

(51) Int. Cl.
*C07J 9/00*   (2006.01)

(52) U.S. Cl.
CPC .................................... *C07J 9/005* (2013.01)

(58) Field of Classification Search
CPC ....................................................... C07J 9/005
See application file for complete search history.

(56) References Cited

U.S. PATENT DOCUMENTS 10,407,462 B2 * 9/2019 Zampella ................. A61P 13/12
10,800,807 B2 * 10/2020 Pellicciari ............ C07J 41/0061
(Continued)

FOREIGN PATENT DOCUMENTS

| CA | 2948585 A1 | 12/2015 |
|---|---|---|
| CN | 106661079 A | 5/2017 |

(Continued)

OTHER PUBLICATIONS

Sharma et al, Bioorganic & Medicinal Chemistry, Bile acid toxicity structure-activity relationships: Correlations between cell viability and lipophilicity in a panel of new and known bile acids using an oesophageal cell line (HET-IA), 2010, 18, pp. 6886-6895. (Year: 2010).*

(Continued)

*Primary Examiner* — Alexander R Pagano
(74) *Attorney, Agent, or Firm* — Nixon Peabody LLP

(57) ABSTRACT

The present application relates to a method for preparing a cholic acid compound. Specifically, the method prepares a compound as shown in formula I, including subjecting a compound of formula 2 to an oxidization reaction to obtain a compound of formula 3; attaching a trimethylsilyl group to the compound of formula 3 to obtain a compound of formula 4; reacting the compound of formula 4 with acetaldehyde to obtain a compound of formula 5; subjecting the compound of formula 5 to a catalytic hydrogenation reaction to obtain a compound of formula 6; and converting a cyano group of the compound of formula 6 to a carboxyl group to give the compound of formula I.

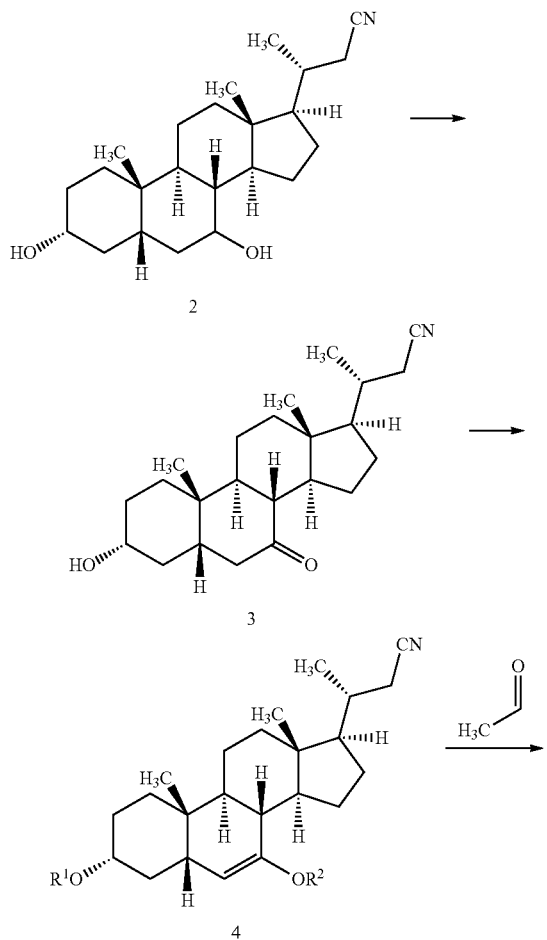

(Continued)

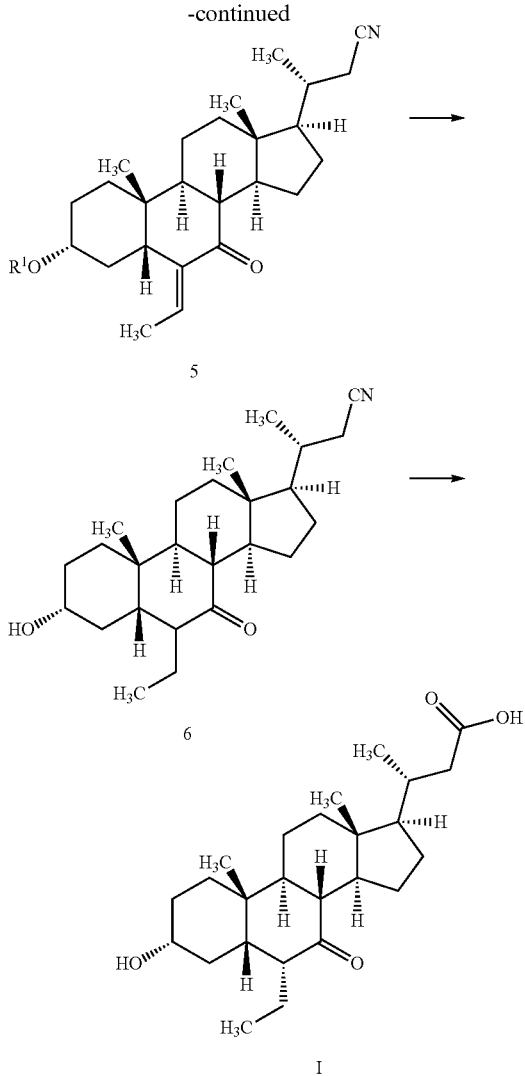

(56) References Cited

U.S. PATENT DOCUMENTS

| | | | |
|---|---|---|---|
| 10,875,888 B2* | 12/2020 | He | A61P 31/14 |
| 2016/0213689 A1* | 7/2016 | Pruzanski | A61P 29/00 |
| 2021/0040140 A1* | 2/2021 | He | A61P 3/04 |

FOREIGN PATENT DOCUMENTS

| | | | |
|---|---|---|---|
| WO | WO 00/37077 | 6/2000 | |
| WO | WO-2004007521 A2 * | 1/2004 | C07J 9/005 |
| WO | WO 2016/173524 A1 | 11/2016 | |

OTHER PUBLICATIONS

D'Amore et al, Journal of Medicinal Chemistry, Design, Synthesis, and Biological Evaluation of Potent Dual Agonists of Nuclear and Membrane Bile Acid Receptors, 2014, 57, pp. 937-954. (Year: 2014).*

Wikipedia, Wikipedia, Nitrile, 2020, pp. 1-12, recovered from https://en.wikipedia.org/wiki/Nitrile on Aug. 26, 2020. (Year: 2020).*

C. Festa et al., 57 Journal of Medicinal Chemistry, 8477-8495 (2014) (Year: 2014).*

International Search Report in International Application No. PCT/CN2018/113326 dated Feb. 13, 2019 (3 pages).

Forman, B.M. et al., "Identification of a Nuclear Receptor That Is Activated by Farnesol Metabolites," Cell 81, pp. 687-693 (1995).

Mangelsdorf, D.J. et al., "The RXR Heterodimers and Orphan Receptors," Cell 83, pp. 841-850 (1995).

Seol, W. et al., "Isolation of Proteins That Interact Specifically with the Retinoid X Receptor: Two Novel Orphan Receptors," Mol. Endocrinnol, 9(1): 72-85 (1995).

D'Amore , C. et al., "Design, Synthesis, and Biological Evaluation of Potent Dual Agonists of Nuclear and Membrane Bile Acid Receptors," J. Med. Chem. 57, pp. 937-954 (2014).

20 Claims, No Drawings

\* cited by examiner

METHOD FOR PREPARING CHOLIC ACID COMPOUND

REFERENCES TO RELATED APPLICATIONS

This application is a U.S. national stage of PCT/CN2018/113326 filed on Nov. 1, 2018, which claims the benefits of the Chinese patent application No. 201711062367.6 filed on Nov. 2, 2017 before the National Intellectual Property Administration P. R. China, the contents of which are all incorporated herein by reference in their entireties.

TECHNICAL FIELD

The present application belongs to the field of pharmaceutical chemistry, and specifically, the present application relates to a method for preparing a cholic acid compound.

BACKGROUND

Farnesoid X receptor (FXR) is an orphan nuclear receptor originally identified from rat liver cDNA libraries (BM. Forman, et al., Cell 81: 687-693 (1995)), which is closely related to insect ecdysone receptors. FXR is a member of the family of ligand-activated transcription factor nuclear receptors, including steroid, retinoid and thyroid hormone receptors (DJ. Mangelsdorf, et al., Cell 83: 841-850 (1995)). It is revealed by Northern and in situ analyses that FXR is abundantly expressed in the liver, intestine, kidney, and adrenal gland (BM. Forman, et al., Cell 81: 687-693 (1995) and W. Seol, et al., Mol. Endocrinnol, 9: 72-85 (1995)). FXR forms a heterodimer with the 9-cis retinoic acid receptor (RXR), thereby binding to DNA. The FXR/RXR heterodimer preferentially binds to a component consisting of two nuclear receptor half-sites of the consensus AG(G/T)TCA, which forms inverted repeats and is separated by one nucleotide (IR-1 motif) (BM. Forman, et al., Cell 81: 687-693 (1995)). However, these compounds fail to activate FXR of mouse and human, making the natural nature of endogenous FXR ligands uncertain. Some naturally occurring cholic acids bind to and activate FXR at physiological concentrations (PCT WO 00/37077, published on Jun. 29, 2000). As such, the cholic acids as the FXR ligands include chenodeoxycholic acid (CDCA), deoxycholic acid (DCA), lithocholic acid (LCA), and taurine and glycine conjugates of these cholic acids.

J. Med. Chem. 2014, 57, 937-954 and WO2016173524 report a compound of formula I which can be used as an intermediate for the preparation of various FXR agonists and a method for preparing the compound:

D'Amore et al. reports the following preparation route in J. Med. Chem. 2014, 57, 937-954:

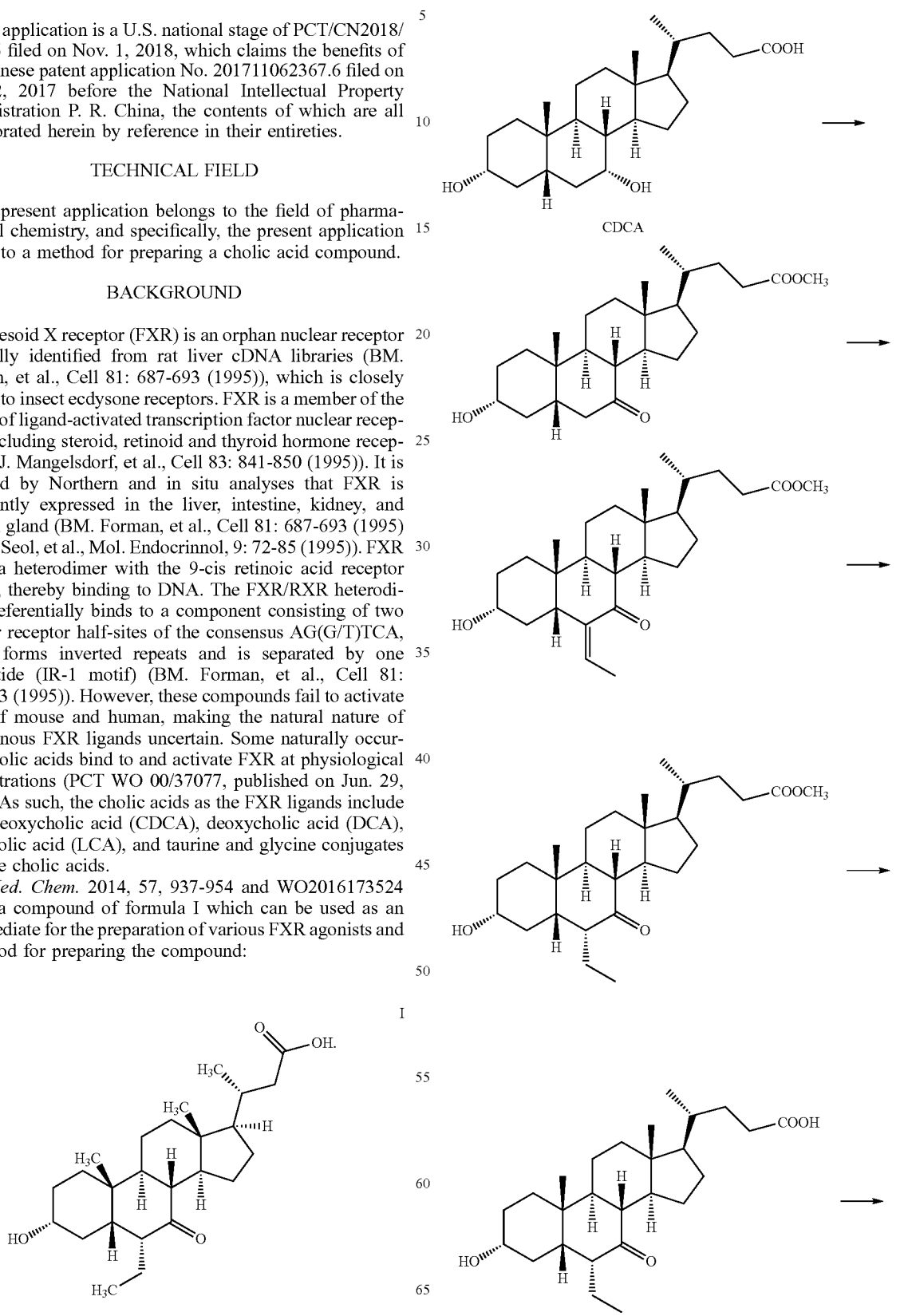

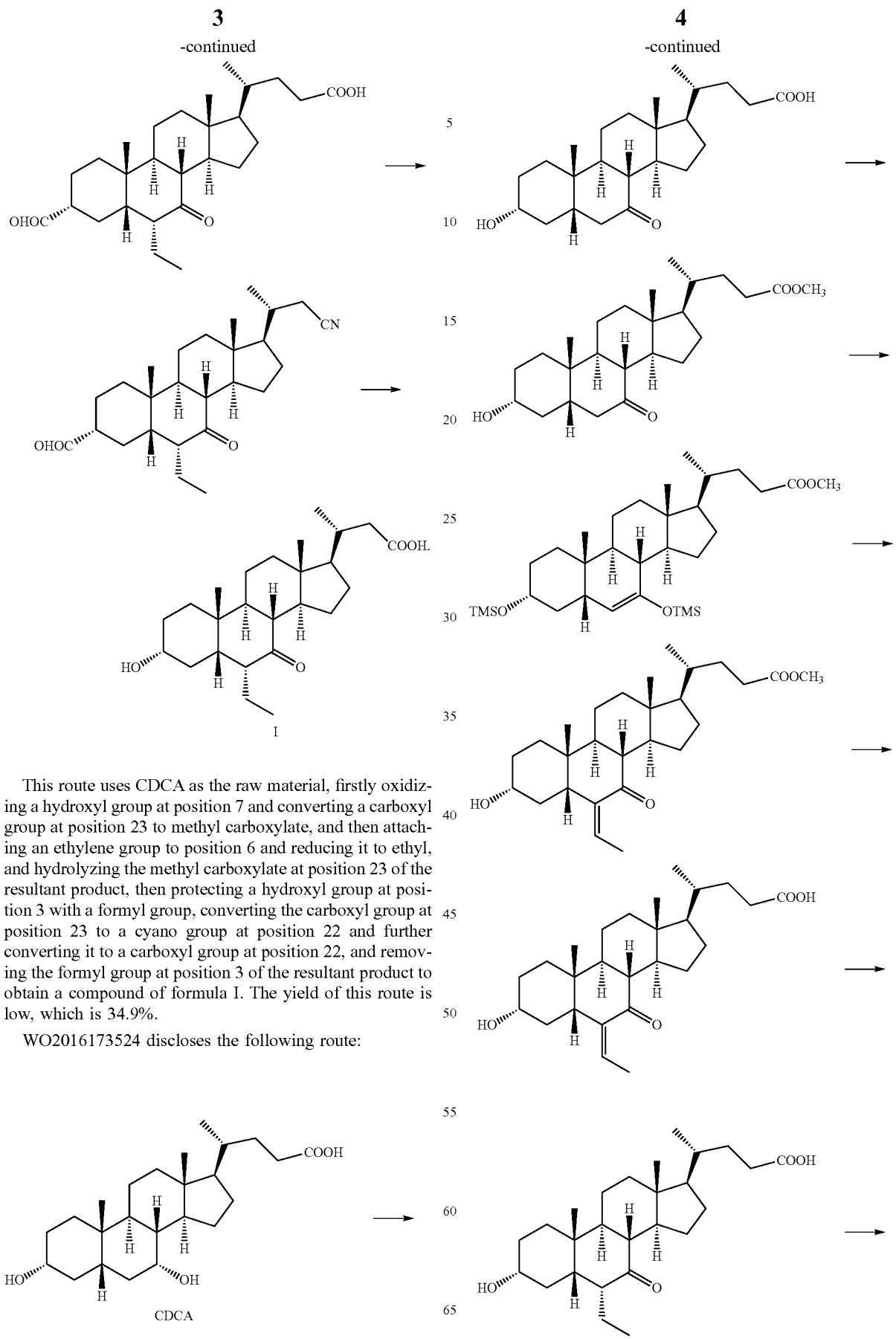

This route uses CDCA as the raw material, firstly oxidizing a hydroxyl group at position 7 and converting a carboxyl group at position 23 to methyl carboxylate, and then attaching an ethylene group to position 6 and reducing it to ethyl, and hydrolyzing the methyl carboxylate at position 23 of the resultant product, then protecting a hydroxyl group at position 3 with a formyl group, converting the carboxyl group at position 23 to a cyano group at position 22 and further converting it to a carboxyl group at position 22, and removing the formyl group at position 3 of the resultant product to obtain a compound of formula I. The yield of this route is low, which is 34.9%.

WO2016173524 discloses the following route:

-continued

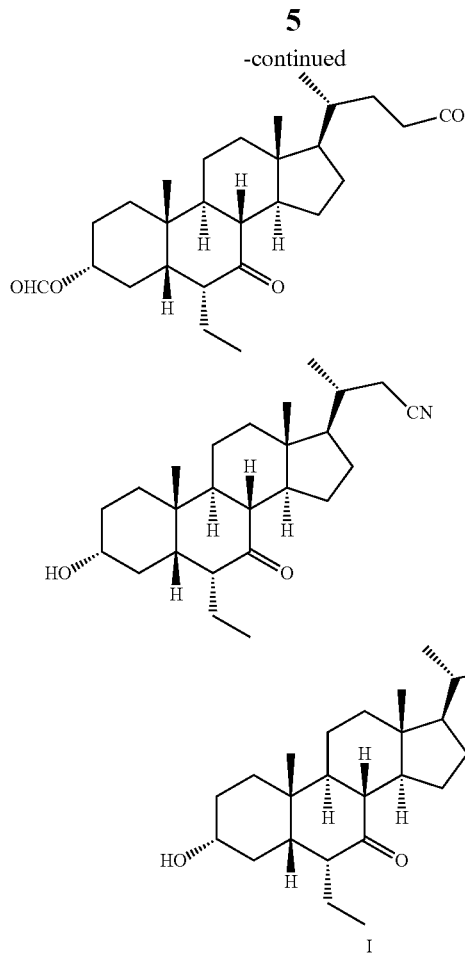

The difference between this route and the route reported by *J. Med. Chem.* 2014, 57, 937-954 is that the sequence of the steps of reducing the ethylene group at position 6 to ethyl and hydrolyzing the methyl carboxylate at position 23 is different. *J. Med. Chem.* 2014, 57, 937-954 is reduction followed by hydrolyzation, while WO2016173524 is hydrolyzation followed by reduction. The yield of the route in WO2016173524 is 13.1%.

Therefore, a preparation route with high yield needs to be developed, so as to suit for industrial application.

SUMMARY OF THE INVENTION

In one aspect, the present application provides a preparation method for a compound of formula I,

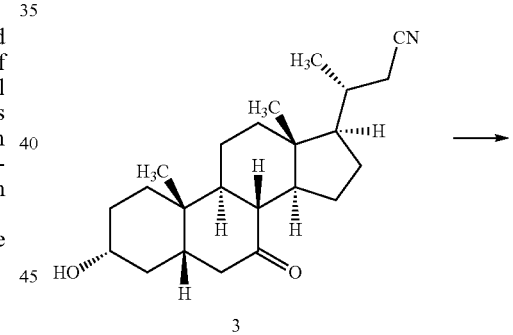

comprising the following steps:

a) subjecting a compound of formula 2 to an oxidization reaction to obtain a compound of formula 3,

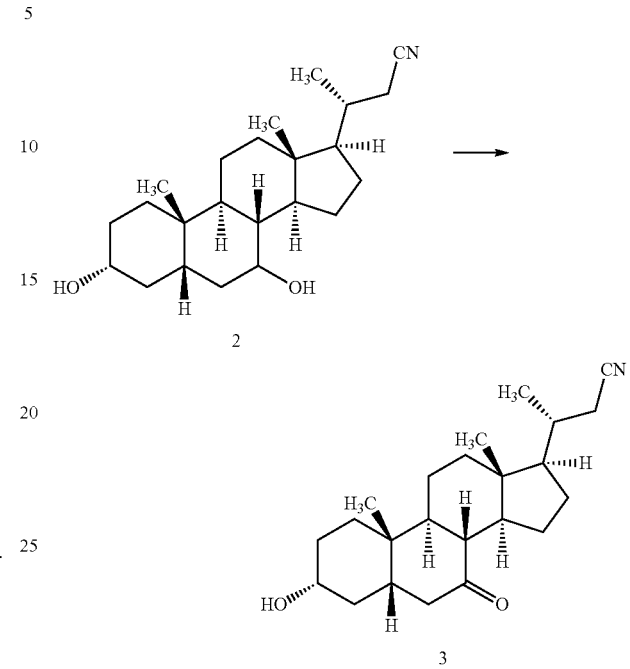

b) attaching a protecting group to the compound of formula 3 to obtain a compound of formula 4,

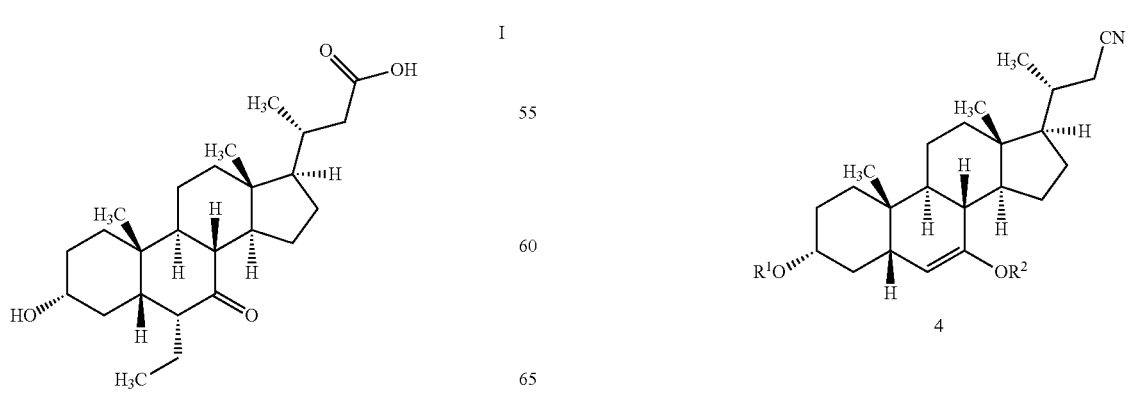

c) reacting the compound of formula 4 with acetaldehyde to obtain a compound of formula 5,

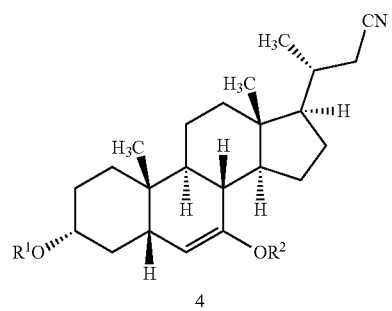

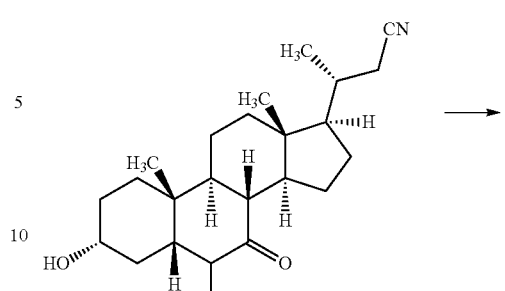

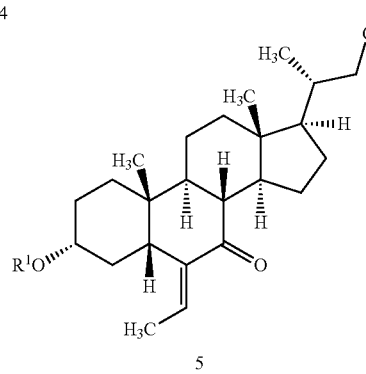

d) subjecting a compound of formula 5 to a reduction reaction to obtain a compound of formula 6,

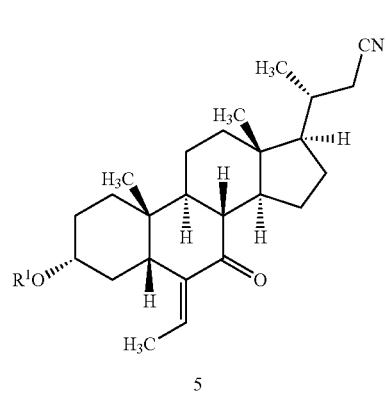

e) converting a cyano group of the compound of formula 6 to a carboxyl group to give the compound of formula I,

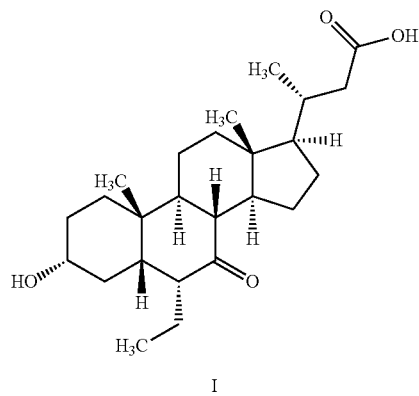

wherein, said $R^1$ and $R^2$ are each independently selected from a silyl ether protecting group.

In another aspect, the present application provides a preparation method for the compound of formula 2 comprising the following steps:

f) attaching a formyl group to a compound of formula 7 to obtain a compound of formula 8,

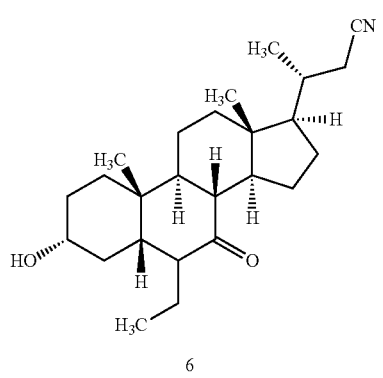

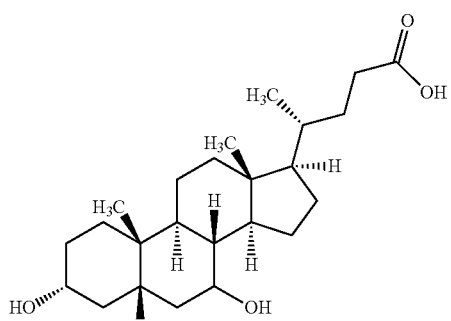

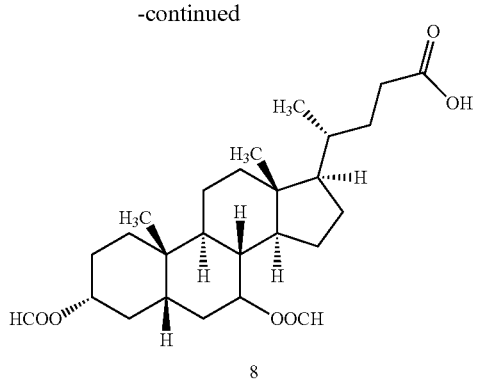

g) converting a carboxyl group at position 23 of the compound of formula 8 to a cyano group at position 22 to obtain a compound of formula 9, and removing a formyl group from the compound of formula 9 to obtain the compound of formula 2,

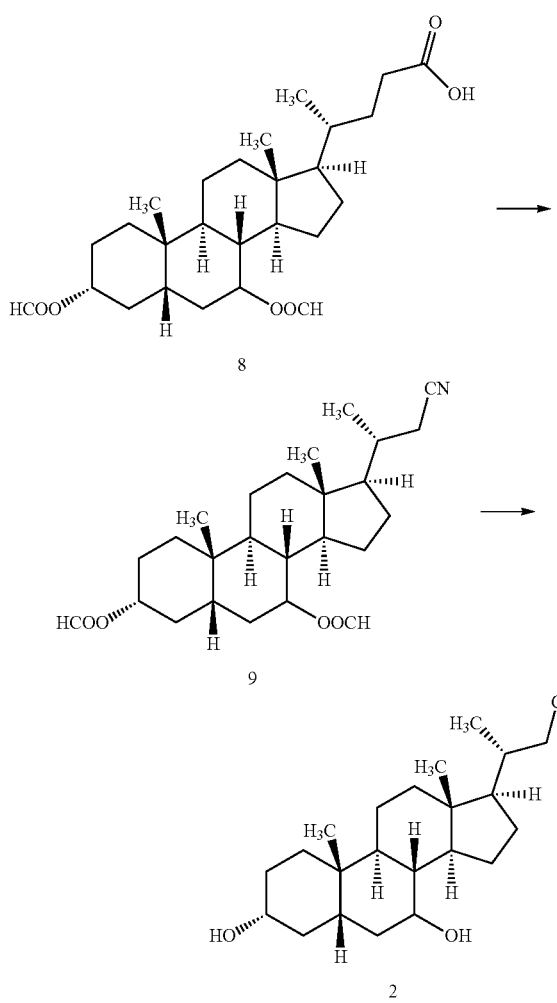

In another aspect, the present application provides a preparation method for the compound of formula I using CDCA as the raw material, which comprises the method for preparing the compound of formula 2 from the compound of formula 7 and the method for preparing the compound of formula I from the compound of formula 2 as described above.

In some embodiments, the silyl ether protecting group is preferably selected from trimethylsilyl (TMS), triethylsilyl (TES), tert-butyldimethylsilyl (TBDMS), or tert-butyldiphenylsilyl (TBDPS), preferably trimethylsilyl (TMS).

In some embodiments, an oxidant used in said step a) is selected from sodium hypochlorite, bromine hypochlorite, N-bromosuccinimide (NBS), N-chlorosuccinimide (NCS), hydrogen peroxide, or potassium dichromate, preferably selected from sodium hypochlorite. In terms of adding amount, a molar ratio of the compound of formula 2 to the oxidant is selected from 1:(1 to 5), preferably 1:(1 to 2), and more preferably 1:1.

In some embodiments, said step a) is performed in the presence of bromine; preferably, the compound providing bromine can be selected from sodium bromide or potassium bromide. In terms of adding amount, a molar ratio of the compound of formula 2 to sodium bromide or potassium bromide is selected from 1:(0.1 to 2), preferably 1:(0.1 to 2) or 1:(0.1 to 0.5), and more preferably 1:0.2.

In some embodiments, a solvent of said step a) is selected from dichloromethane, methanol, ethanol, propanol, diethyl ether, isopropyl ether, tetrahydrofuran, methyl tert-butyl ether, ethyl acetate, acetonitrile, acetone, or a mixed solvent thereof, preferably selected from dichloromethane, methanol, ethyl acetate, or a mixed solvent thereof.

In some embodiments, said step a) is performed in the presence of an organic acid, which is selected from formic acid, acetic acid, propionic acid, citric acid or malic acid, preferably formic acid, acetic acid or propionic acid.

In some embodiments, a reaction temperature of said step a) is selected from $-50°$ C. to $50°$ C., preferably $-30°$ C. to $40°$ C., and more preferably $-20°$ C. to $40°$ C.

In some embodiments, said step b) is performed in the presence of an alkali metal cationic organic base, which is selected from lithium diisopropylamide (LDA), n-butyl lithium (nBuLi), sodium diisopropylamide, potassium diisopropylamide, sodium hexamethyldisilazide, potassium hexamethyldisilazide or lithium hexamethyldisilazide, preferably LDA.

In some embodiments, said step b) is performed in the presence of an acid-binding agent, which is selected from triethylamine, diisopropylethylamine, tributylamine or pyridine, preferably triethylamine.

In some embodiments, said step b) is performed under the protection of an inert gas, which is selected from nitrogen.

In some embodiments, a solvent of said step b) is selected from n-heptane, n-hexane, tetrahydrofuran, methyl tert-butyl ether or toluene, preferably tetrahydrofuran.

In some embodiments, a reaction temperature of said step b) is selected from $-90°$ C. to $-50°$ C., preferably $-85°$ C. to $-60°$ C., and more preferably $-80°$ C. to $-70°$ C.

In some embodiments, said step c) is performed in the presence of boron trifluoride, aluminum trichloride, iron trichloride, zinc chloride, tin tetrachloride or niobium pentachloride, preferably boron trifluoride.

In some embodiments, a solvent of said step c) is selected from n-heptane, n-hexane, tetrahydrofuran, methyl tert-butyl ether, toluene or dichloromethane, preferably dichloromethane.

In some embodiments, a reaction temperature of said step c) is selected from $-90°$ C. to $-50°$ C., preferably $-75°$ C. to $-55°$ C.

In some embodiments, said step b) is performed under the protection of an inert gas, which is selected from nitrogen.

In some embodiments, a catalyst of said step d) is selected from Pd/C, Pt/C, Rh/C, Pd(OH)$_2$, Raney Ni or PtO$_2$, preferably Pd/C.

In some embodiments, H$_2$ pressure of said step d) is selected from 1.0 to 3.0 MPa, preferably 1.5 to 2.5 MPa.

In some embodiments, a solvent of said step d) is selected from methanol, ethanol, propanol or tetrahydrofuran, preferably methanol or tetrahydrofuran.

In some embodiments, a reaction temperature of said step d) is selected from 30° C. to 70° C., preferably 40° C. to 60° C., and more preferably 45° C. to 55° C.

In some embodiments, said step e) is performed in the presence of NaOH or KOH, preferably NaOH.

In some embodiments, a reaction solvent of said step e) is a mixed solvent of water and one or more selected from methanol, ethanol, propanol or butanol, preferably a mixed solvent of water and one or more selected from ethanol, propanol or butanol, more preferably a mixed solvent of ethanol and water, and more preferably a mixed solvent of ethanol and water in a volume ratio of 1:1.

In some embodiments, a reaction temperature of said step e) is selected from 60° C. to 125° C., preferably 70° C. to 115° C.

In some embodiments, the reaction temperature of said step e) is selected from 60° C. to 78° C., preferably 70° C. to 78° C.

In some embodiments, said step f) is performed in formic acid.

In some embodiments, a temperature of the reaction step f) is selected from 30° C. to 60° C., preferably 40° C. to 50° C.

In some embodiments, in the reaction step g), the compound of formula 8 is converted to the compound of formula 9 in the presence of trifluoroacetic acid and trifluoroacetic anhydride.

In some embodiments, in the reaction step g), the compound of formula 8 is converted to the compound of formula 9 in the presence of sodium nitrite or potassium nitrite.

In some embodiments, a reaction temperature of the reaction step g) for converting the compound of formula 8 to the compound of formula 9 is selected from −10° C. to 40° C., preferably −10° C. to 10° C., and more preferably −5° C. to 5° C.

In some embodiments, a reaction of removing the formyl group from the compound of formula 9 to obtain the compound of formula 2 in the reaction step g) is performed in an aqueous solution of NaOH or KOH, preferably the aqueous solution of NaOH.

Definitions and Terms

Unless otherwise stated, the terms and phrases used herein have the meanings listed below. A particular term or phrase should not be considered as being indefinite or unclear in the absence of a specific definition, but should be interpreted according to the meaning generally understood by those skilled in the art. When a trade name appears herein, it is intended to refer to corresponding commodity or active ingredient thereof.

In the present application, the protecting group and the method for attaching or removing the same can be achieved by using a conventional method in the art, and the method can be one-step reaction or multi-step reaction, such as, but not limited to, referring to Greene's Protective Groups in Organic Synthesis-4th Edition published by Wiley Press, or Protecting Groups published by Chemical Industry Press.

In the present application, the compounds may exist in specific geometric or stereoisomeric forms. All such compounds envisaged in the present application include cis and trans isomers, (−)- and (+)-enantiomers, (R)- and (S)-enantiomers, diastereomers, (D)-isomers, (L)-isomers, and racemic mixtures and other mixtures thereof, such as enantiomeric or diastereomeric excess mixtures, and all of these mixtures fall within the scope of the present application. Additional asymmetric carbon atoms may be present in the substituents such as alkyl. All these isomers and mixtures thereof are included in the scope of the present invention.

In the present application, the protecting group and the method for attaching or removing the same can be achieved by using a conventional method in the art, and the method can be one-step reaction or multi-step reaction, such as, but not limited to, referring to Greene's Protective Groups in Organic Synthesis-4th Edition published by Wiley Press, or Protecting Groups published by Chemical Industry Press.

In this application, the atoms of a steroid compound can be numbered according to the common knowledge in the field, such as, but not limited to referring to Fundamental Organic Chemistry-3rd Edition edited by Qiyi XING and published by Higher Education Press. In the present application, taking the CDCA compound for example, some atom numbers thereof are marked as follows:

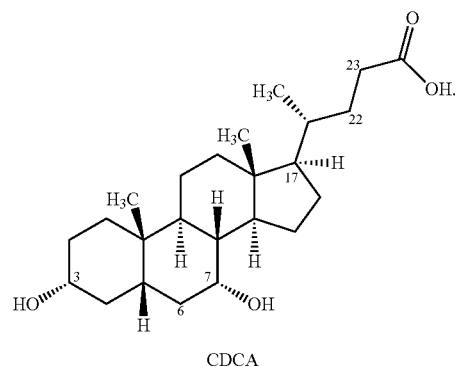

CDCA

In the present application, compounds of formula 2 in which position 7 is in the α configuration or β configuration both can be used as the raw material for reaction to obtain the compound of formula I. Correspondingly, both chenodeoxycholic acid (CDCA) and ursodeoxycholic acid (UDCA) can be used as the raw material for preparing the compound of formula 2 according to the method provided in the present application.

Advantageous Effect

The preparation route of the present application has high yield, requires less purification operations, and is suitable for industrial application.

DETAILED DESCRIPTION OF THE INVENTION

For better understanding the content of the present invention, the following detailed description is made in combination with the specific examples, but the specific examples are not intended to limit the content of the present invention.

Preparation Example 1

Preparation of the Compound of Formula I

Step 1-1 Preparation of the Compound of Formula 3

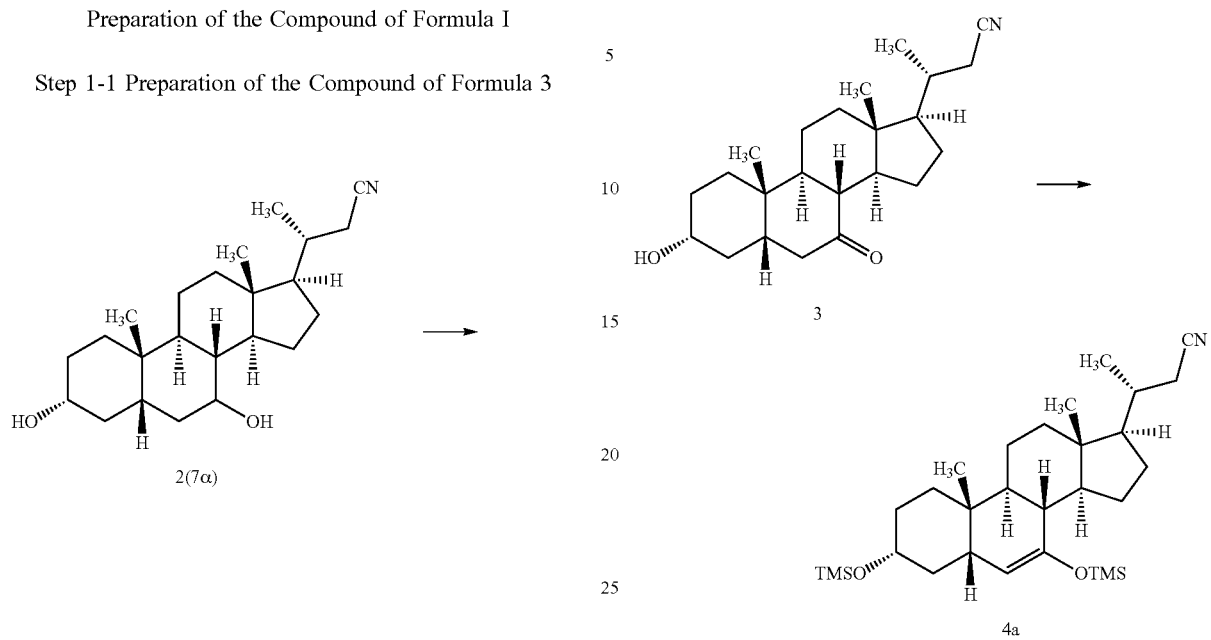

130 mL of dichloromethane, 130 mL of methanol, 390 mL of AcOH, and 130 g of the compound of formula 2 (7α) were added into a reaction flask and stirred to dissolve. 130 mL of aqueous solution of 7.4 g of sodium bromide was added thereto, followed by being cooled down to −30° C. to −20° C., and 268 g of 10% sodium hypochlorite solution was added dropwise. The reaction was monitored by TLC until completed, and an aqueous solution of sodium sulfite (20%) was added thereto. The organic layer was separated, and the aqueous layer was extracted with dichloromethane. The organic phases were combined, washed with purified water, and adjusted to pH 7-8 by adding 15% sodium carbonate aqueous solution. The organic phase was separated, washed with saturated brine, dried over anhydrous sodium sulfate, and concentrated to dryness under reduced pressure at 45° C. to obtain the compound of formula 3. The crude product was refluxed by adding 650 mL of ethyl acetate, cooled down to crystallize, and subjected to air pump filtration, and the filter cake was blast dried at 60° C. for 12 h to obtain 114.5 g of the compound of formula 3. The yield was 88.6%. MS: m/z: 358.40 (M+), 340.36 (M−18), 322.36 (M−2×18).

Step 1-2 Preparation of a Compound of Formula 4a

1 L of tetrahydrofuran and 129 g of the compound of formula 3 were added into a reaction flask, and stirred to dissolve at room temperature. Then 235 g of trimethylchlorosilane was added thereto, followed by being cooled down to −70° C. under the protection of nitrogen. LDA (2M) was added dropwise while the temperature was maintained at −70° C. or less, and it was stirred for 0.5 h at a temperature of −70° C. or less after adding. 255 g of triethylamine was added dropwise, which was stirred for 2 h at the same temperature after adding. The reaction was monitored by TLC until completed, followed by being heated up to −30° C. to −20° C., and 1350 g of sodium bicarbonate solution (9%) was added dropwise, which was stirred at 0° C. to 10° C. for 1 h after adding. The organic layer was separated, and the aqueous phase was extracted with ethyl acetate. The organic phases were combined, washed with 1.2 L of sodium bicarbonate solution (5%), 1.2 L of purified water, and 1.2 L of saturated brine successively, dried over anhydrous sodium sulfate and filtered, and the filtrate was concentrated to dryness under reduced pressure at 50° C. to obtain an orange-yellow semi-solid, which was directly used for the next step.

Step 1-3 Preparation of a Compound of Formula 5a

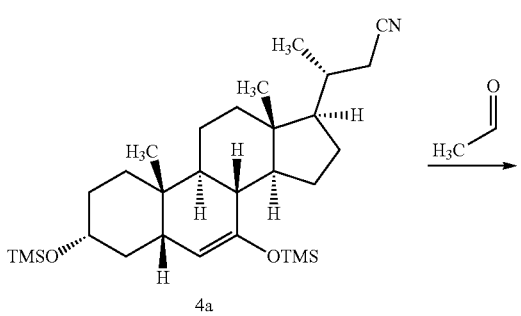

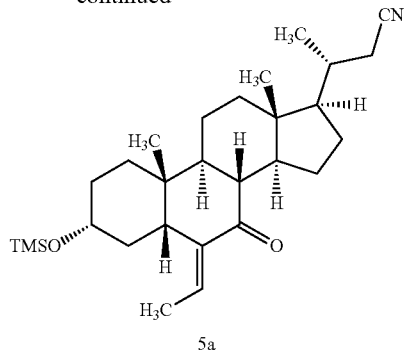

5a 108 mL of dichloromethane and 18.0 g of the compound of formula 4a were added into a reaction flask, and cooled down to a temperature of −75° C. or less under the protection of nitrogen, to which 5.2 mL of acetaldehyde was added, and 40 mL of boron trifluoride diethyl etherate was added dropwise when controlling a temperature at −70° C. or less, followed by being stirred for 2 h when maintaining a temperature at −60° C. or less after adding. The reaction was monitored by TLC until completed, followed by being heated up to 0° C. and stirred for 1 h. 300 g of sodium bicarbonate solution (9%) was added dropwise and stirred for 30 min. The organic layer was separated, and the aqueous phase was extracted with dichloromethane. The organic phases were combined, washed with 5% sodium bicarbonate solution, purified water, and saturated brine successively, dried over sodium sulfate and filtered, and the filtrate was concentrated to dryness under reduced pressure at 40° C. to 50° C. to obtain an orange-yellow foamed solid, which was directly used for the reaction of the next step. MS: m/z: 456.42 (M+), 438.44 (M−18).

Step 1-4 Preparation of the Compound of Formula 6

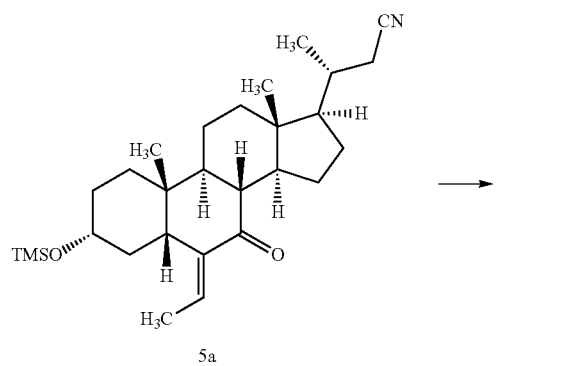

40 g of the compound of formula 5a was added into 200 mL of methanol, and stirred to dissolve at room temperature, to which 10 g of palladium-carbon (5%) was added, stirred well, and transferred to an autoclave. A reaction was performed with the hydrogen pressure being increased to 1.5 to 2.5 MPa and the temperature being increased to 50° C., until the hydrogen pressure no longer decreased. The reaction was monitored by TLC until completed. The reaction solution was transferred out after being replaced with nitrogen, the palladium-carbon was removed by filtration and the filtrate was concentrated to dryness under reduced pressure. The yield was above 100% and the product was directly used for the next step. MS: m/z: 386.45 (M+), 368.41 (M−18).

Step 1-5 Preparation of the Compound of Formula I

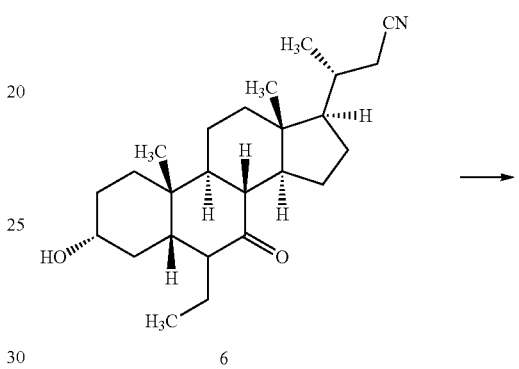

6

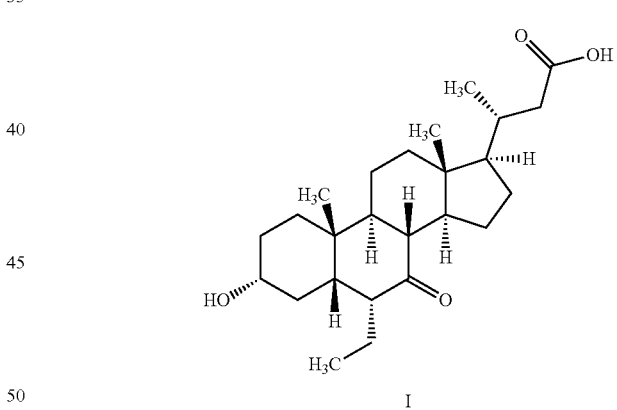

I 52 g of sodium hydroxide was dissolved in 100 mL of water, to which 100 mL of ethanol and 10 g of the compound of formula 6 were added, followed by being heated to perform a reflux reaction. The reaction was monitored by TLC until completed, followed by being cooled down to room temperature and concentrated under reduced pressure to remove the ethanol. The pH was adjusted to 2-3 with hydrochloric acid. 100 mL of ethyl acetate was added and stirred to dissolve. The organic phase was separated, and the aqueous phase was extracted with ethyl acetate. The organic phases were combined, washed with saturated brine, dried over sodium sulfate, and concentrated to dryness under reduced pressure to obtain 9.8 g of the compound of formula I. The yield was 93.3% (combined yield of steps 1-2 to 1-5). MS: m/z: 405.51 (M+), 387.49 (M−18).

Preparation Example 2

Preparation of the Compound of Formula 2

Step 2-1 Preparation of the Compound of Formula 8

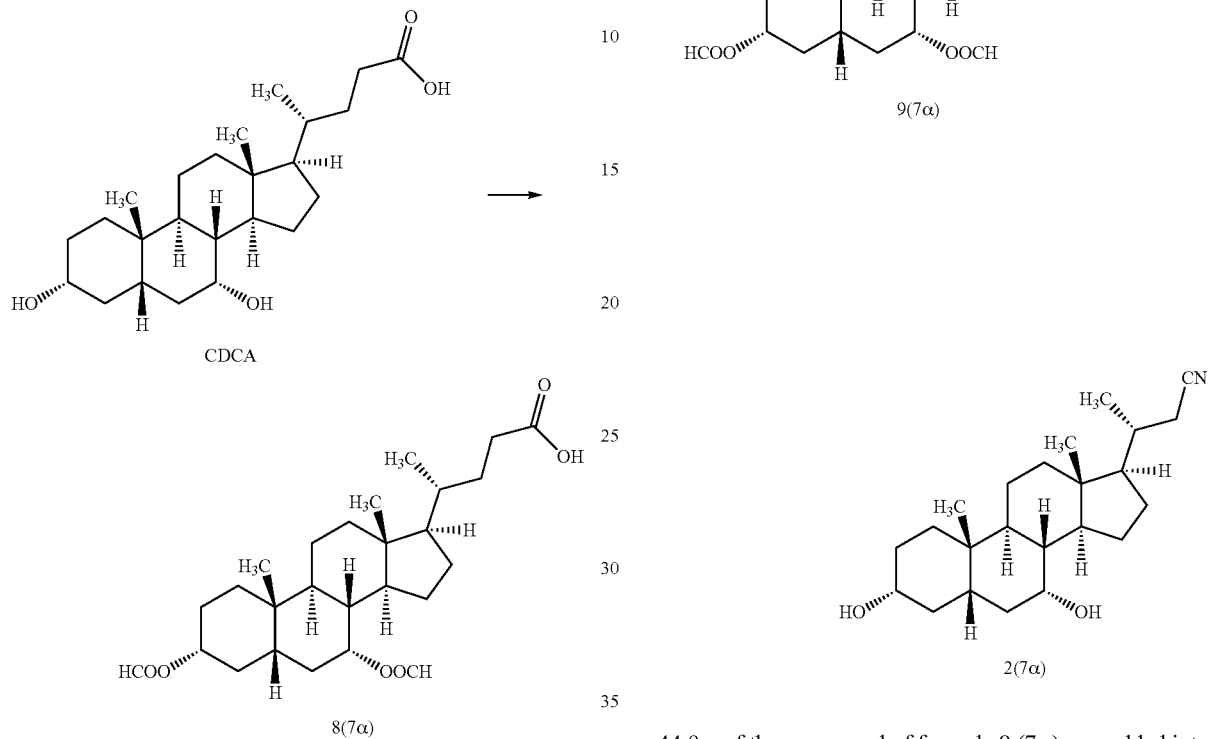

200 g of chenodeoxycholic acid (CDCA) was added into 1 L of formic acid, and stirred and heated up to 40° C. to 50° C. The reaction of the raw materials was monitored by TLC until completed, followed by being cooled down to crystallize, and being subjected to air pump filtration, and the filter cake was added with 2 L of purified water and stirred for 1 h at room temperature, subjected to air pump filtration, and blast dried at 70° C. to obtain 198.1 g of the compound of formula 8 (7α). The yield was 86.7%.

Step 2-2 Preparation of the Compound of Formula 2 (7α)

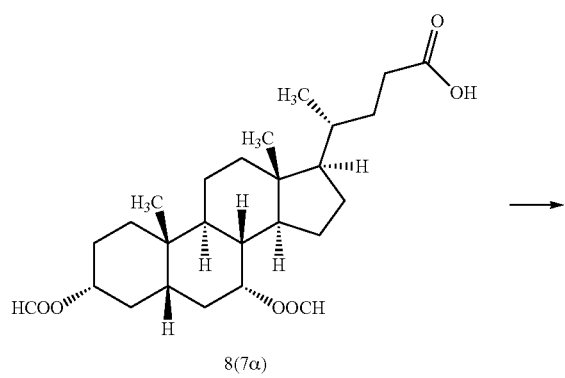

44.9 g of the compound of formula 8 (7α) was added into a mixed solution of 135 mL of trifluoroacetic acid and 168 g of trifluoroacetic anhydride, stirred and cooled down to −5° C. to 5° C., and 10.3 g of sodium nitrite was added in portions. After adding, it was stirred under a temperature maintained at −5° C. to 5° C. for 1 h, and then heated up to 40° C. for reaction. The reaction was monitored by TLC, and it was cooled down after the reaction. The reaction solution was added dropwise into 640 g of aqueous solution (20%) of sodium hydroxide. Afterward, it was filtered and the filter cake was added into 160 g of aqueous solution (15%) of sodium hydroxide, to which 90 mL of ethanol was added and a reaction is performed at 50° C. The reaction was monitored by TLC until completed, and the ethanol was removed by concentration under reduced pressure. The remaining reaction solution was extracted with 135 mL of ethyl acetate. The organic phases were combined and washed with sodium hydroxide aqueous solution (5%), hydrochloric acid (1 mol/L), and saturated brine, dried over sodium sulfate, and concentrated to dryness under reduced pressure at 50° C. to obtain the crude product of the compound of formula 2 (7α).

The crude product was added with 90 mL of ethyl acetate, stirred at 55° C. for 2 h, cooled down to room temperature and stirred to crystallize, and subjected to air pump filtration, and the filter cake was blast dried to obtain 30.5 g of an off-white solid, which was the compound of formula 2 (7α). The yield was 84.7%. MS: m/z: 342.43 (M−18), 324.38 (M−2×18).

What is claimed is:

1. A preparation method for a compound of formula I,

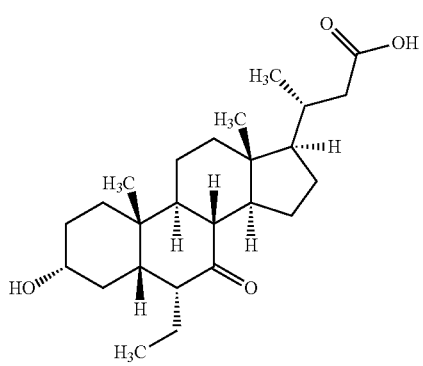

comprising the following steps:
   a) subjecting a compound of formula 2 to an oxidization reaction in a solvent to obtain a compound of formula 3,

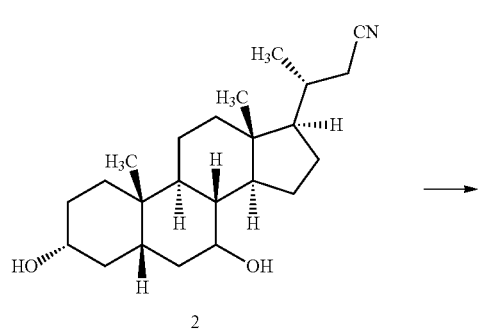

b) attaching a protecting group to the compound of formula 3 in a solvent to obtain a compound of formula 4,

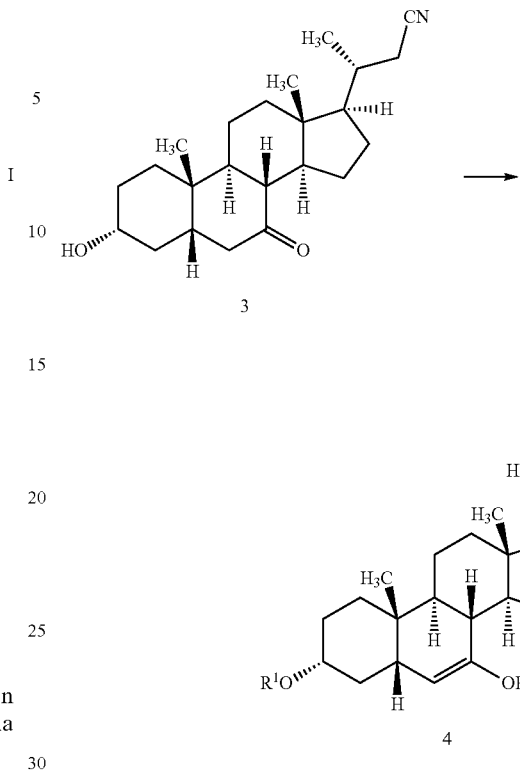

c) reacting the compound of formula 4 with acetaldehyde in a solvent to obtain a compound of formula 5,

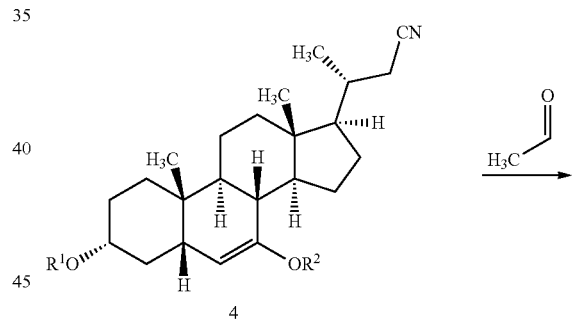

d) subjecting the compound of formula 5 to a reduction reaction in a solvent under a catalyst to obtain a compound of formula 6,

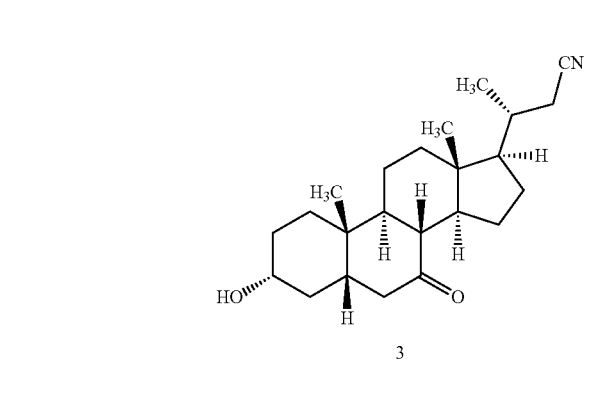

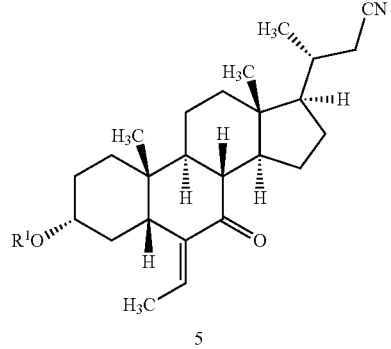

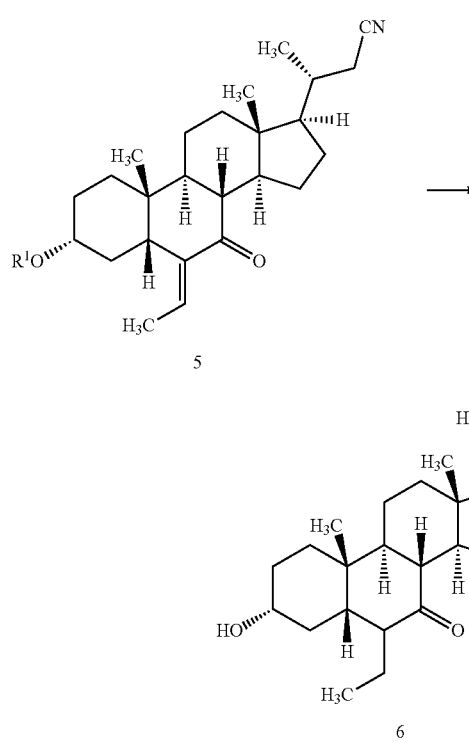

5

6 e) converting cyano group of the compound of formula 6 to a carboxyl group to give the compound of formula I,

6

I wherein, said $R^1$ and $R^2$ are each independently selected from a silyl ether protecting group.

2. The preparation method of claim 1, wherein the preparation method for the compound of formula 2 comprises the following steps:

f) attaching a formyl group to a compound of formula 7 to obtain a compound of formula 8,

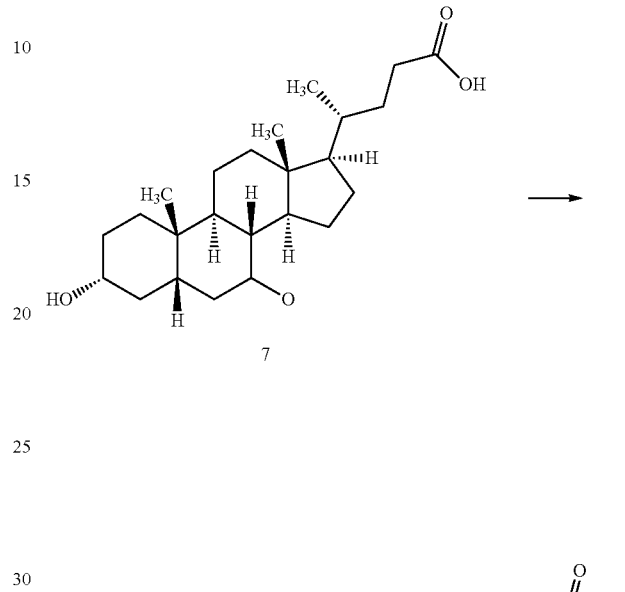

7

8 g) converting a carboxyl group at position 23 of the compound of formula 8 to a cyano group at position 22 to obtain a compound of formula 9, and removing a formyl group from the compound of formula, 9 to obtain the compound of formula 2,

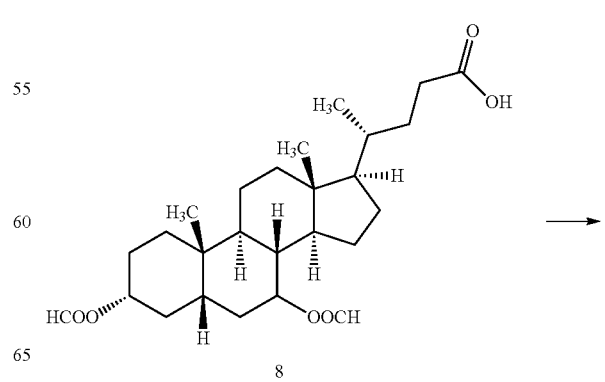

8

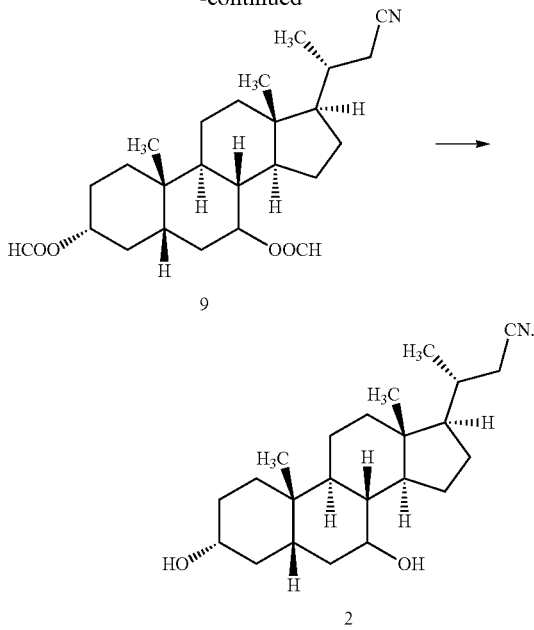

3. The preparation method of claim 1, wherein the silyl ether protecting group is selected from trimethylsilyl, triethylsilyl, tert-butyldimethylsilyl, or tert-butyldiphenylsilyl.

4. The preparation method of claim 1, wherein an oxidant used in said step a) is selected from sodium hypochlorite, bromine hypochlorite, N-bromosuccinimide, N-chlorosuccinimide, hydrogen peroxide or potassium dichromate.

5. The preparation method of claim 4, wherein in said step a, the molar ratio of the compound of formula 2 to the oxidant is selected from 1:(1 to 5).

6. The preparation method of claim 1, wherein said step a) is performed in the presence of bromine.

7. The preparation method of claim 1, wherein the solvent of said step a) is selected from dichloromethane, methanol, ethanol, propanol, diethyl ether, isopropyl ether, tetrahydrofuran, methyl tert-butyl ether, ethyl acetate, acetonitrile, acetone, or a mixed solvent thereof.

8. The preparation method of claim 1, wherein said step a) is performed in the presence of an organic acid, which is selected from formic acid, acetic acid, propionic acid, citric acid or malic acid.

9. The preparation method of claim 1, wherein said step b) is performed in the presence of an alkali metal cationic organic base, which is selected from lithium diisopropylamide, n-butyllithium, sodium diisopropylamide, potassium diisopropylamide, sodium hexamethyldisilazide, potassium hexamethyldisilazide or lithium hexamethyldisilazide.

10. The preparation method of claim 1, wherein said step b) is performed in the presence of an acid-binding agent, which is selected from triethylamine, diisopropylethylamine, tributylamine or pyridine.

11. The preparation method of claim 1, wherein said step c) is performed in the presence of boron trifluoride; aluminum trichloride, iron trichloride, zinc chloride, tin tetrachloride or niobium pentachloride.

12. The preparation method of claim 1, wherein the catalyst of said step d) is selected from Pd/C, PVC, Pt/C, Rh(OH)$_2$, Raney Ni, or PtO$_2$.

13. The preparation method of claim 1, wherein said step e) is performed in the presence of NaOH or KOH.

14. The preparation method of claim 2, Wherein said step f is performed in formic acid.

15. The preparation method of claim 2, wherein in said step g), the compound of formula 8 is converted to the compound of formula 9 in the presence of trifluoroacetic acid or trifluoroacetic anhydride, and sodium nitrite or potassium nitrite.

16. The preparation method of claim 1, wherein said step a) is performed in the presence of sodium bromide or potassium bromide.

17. The preparation method of claim 1 wherein the solvent of said step b) is selected from n-heptane, n-hexane, tetrahydrofuran, methyl tert-butyl ether or toluene.

18. The preparation method of claim 1, wherein the solvent of said step c) is selected from n-heptane, n-hexane, tetrahydrofuran; methyl tert-butyl ether, toluene or dichloromethane.

19. The preparation method of claim 1, wherein the solvent of said step d) is selected from methanol, ethanol, propanol or tetrahydrofuran.

20. The preparation method of claim 2, wherein in step g), a reaction of removing the formyl group from the compound of formula 9 is performed in an aqueous solution of NaOH or KOH.

* * * * *

UNITED STATES PATENT AND TRADEMARK OFFICE
CERTIFICATE OF CORRECTION

PATENT NO. : 11,111,265 B2
APPLICATION NO. : 16/759134
DATED : September 7, 2021
INVENTOR(S) : Zhang et al.

Page 1 of 1

It is certified that error appears in the above-identified patent and that said Letters Patent is hereby corrected as shown below:

In the Claims

At Column 21, Line 32 (Claim 1, approximately Line 22), please delete "converting cyano group of the compound" and insert --converting the cyano group of the compound-- therefor.

At Column 24, Lines 17-18 (Claim 12, Lines 2-3), please delete "selected from Pd/C, PVC, Pt/C, Rh(OH)$_2$" and insert --selected from Pd/C, Pt/C, Rh/C, Pd(OH)$_2$-- therefor.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*